US007962489B1

(12) United States Patent
Chiang et al.

(10) Patent No.: US 7,962,489 B1
(45) Date of Patent: Jun. 14, 2011

(54) INDEXING USING CONTIGUOUS, NON-OVERLAPPING RANGES

(75) Inventors: David Chiang, Saratoga, CA (US); James D. Candlin, Menlo Park, CA (US); Kelvin Soo, Fremont, CA (US)

(73) Assignee: Sage-N Research, Inc., San Jose, CA (US)

( * ) Notice: Subject to any disclaimer, the term of this patent is extended or adjusted under 35 U.S.C. 154(b) by 1086 days.

(21) Appl. No.: 10/982,087

(22) Filed: Nov. 4, 2004

Related U.S. Application Data

(60) Provisional application No. 60/586,544, filed on Jul. 8, 2004.

(51) Int. Cl.
*G06F 17/30* (2006.01)
*C07K 1/00* (2006.01)

(52) U.S. Cl. ........................................ 707/741; 707/941
(58) Field of Classification Search .................... 702/19; 707/737, 742, 741, 941
See application file for complete search history.

(56) References Cited

U.S. PATENT DOCUMENTS

| 5,538,897 | A | | 7/1996 | Yates, III et al. | |
| 5,761,652 | A | * | 6/1998 | Wu et al. ............................ | 707/2 |
| 6,017,693 | A | | 1/2000 | Yates, III et al. | |
| 2002/0184253 | A1 | * | 12/2002 | Agarwal et al. ............... | 707/206 |
| 2005/0165750 | A1 | * | 7/2005 | Shakib et al. ...................... | 707/3 |

OTHER PUBLICATIONS

Oracle Text Application Developer's Guide Release 9.2, 2002.*
Content Based Image Retrieval Systems: A survey, Oct. 2002.*
The Authoritative Dictionary of IEEE Standards Terms, 7th Ed., 2000, p. 1176.*
Franklin, How Operating Systems Work, 2003, pp. 1-14.*
Benson et al.: "GenBank", National Center for Biotechnology Information, Oct. 13, 1999, pp. 15-18.
Aebersold et al.: "Mass Spectrometry in Proteomics", 2001 American Chemical Society, Jan. 23, 2001, pp. 269-295.
Henzel et al.: "Identifying Proteins From Two-Dimensional Gels by Molecular Mass Searching of Peptide Fragments in Protein Sequence Databases", Proc. Natl. Acad. Sci. USA, vol. 90, Jun. 1993, pp. 5011-5015.
Hunt et al.: "Protein Sequencing by Tandem Mass Spectrometry", Proc. Natl. Acad. Sci. USA, vol. 83, Sep. 1986 , pp. 6233-6237.
Brooksbank et al.: "The European Bioinformatics Institute's Data Resources", 2003 Oxford University Press, Nucleic Acids Research, 2003, vol. 31, No. 1, pp. 43-50.
"The BLAST Databases", Jul. 21, 2003, pp. 1-6.
"Swiss-Prot Protein Knowledgebase Release 44.0 Statistics", Jul. 7, 2004, pp. 1-14.

(Continued)

*Primary Examiner* — James Trujillo
*Assistant Examiner* — Albert Phillips
(74) *Attorney, Agent, or Firm* — Bener, Hoffman & Harms, LLP; Jeanette S. Harms

(57) ABSTRACT

A method of efficiently constructing and using an index for searches in large datasets is provided. In this method, a dataset can be divided into a plurality of "buckets", i.e. contiguous, non-overlapping ranges of values of a chosen attribute of elements of the dataset. These buckets can be used to construct discrete index segments. Static index segments (associated with "static" buckets including the more frequently occurring values) are always computed, whereas dynamic index segments (associated with "dynamic" buckets including the less frequently occurring values) can be generated on an as-needed basis and based on the availability of system resources. Thus, search time and storage area can be advantageously reduced because less of the complete index needs to be generated and used.

13 Claims, 7 Drawing Sheets

OTHER PUBLICATIONS

Pappin et al.: "Rapid Identification of Proteins by Peptide-Mass Fingerprinting", Current Biology 1993, vol. 3, No. 6, pp. 327-332.
Aritcle entitled: "TurboSEQUEST Protein Identification Software", Copyright 2000 Thermo Finnigan Corporation, pp. 1-8.
Eng et al.: "An Approach to Correlate Tandem Mass Spectral Data Of Peptides With Amino Acid Sequences In A Protein Database", 1994 American Society For Mass Spectrometry, pp. 976-988.
Article entitled: "Identification of Common Molecular Subsequences", 1980 Academic Press Inc. (London) Ltd., J. Mol. Biol. (1981), 147, pp. 195-197.
Altschul et al.: "Basic Local Alignment Search Tool", J. Mol. Biol. (1990), 215, pp. 403-410.

* cited by examiner

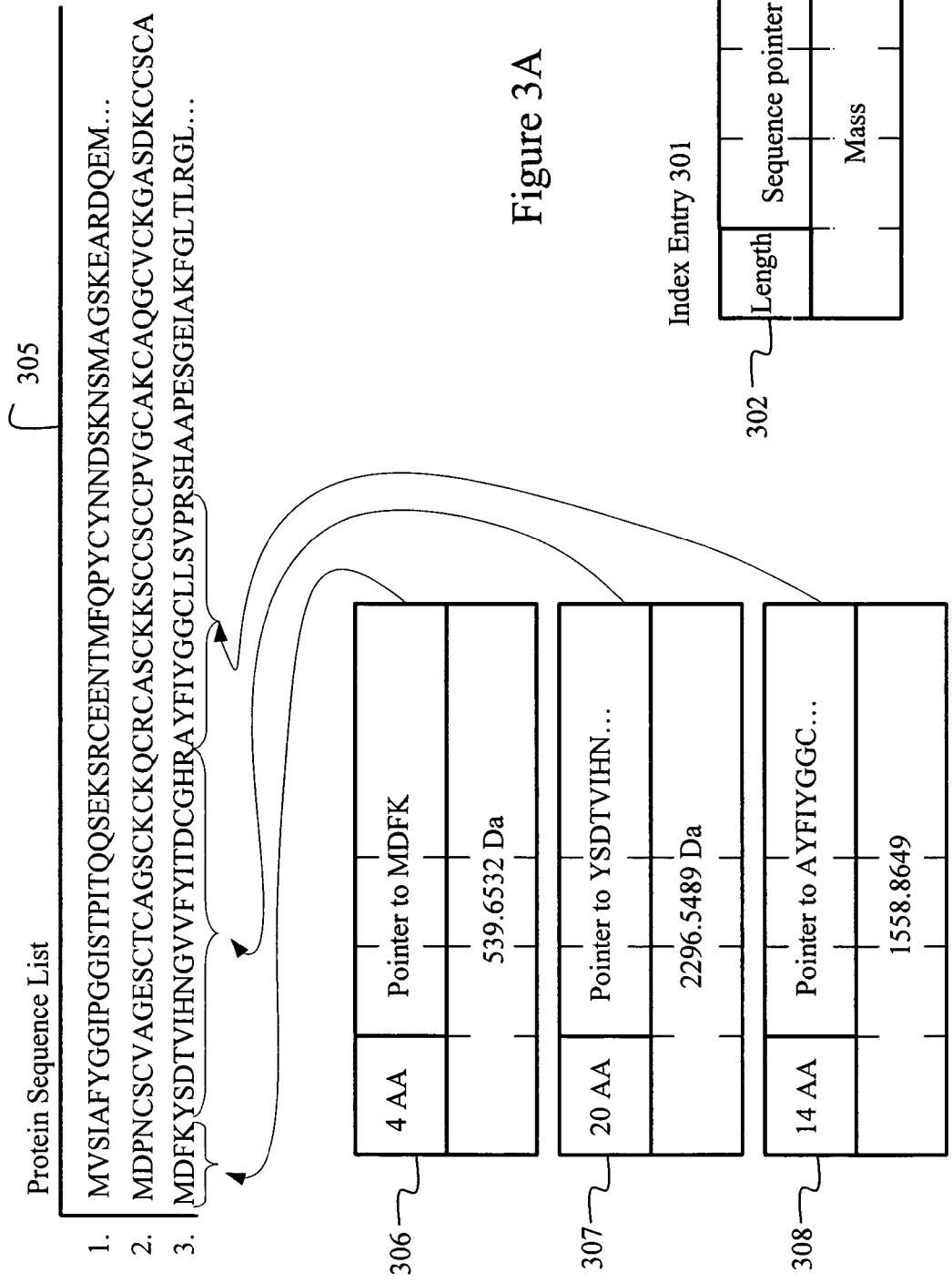

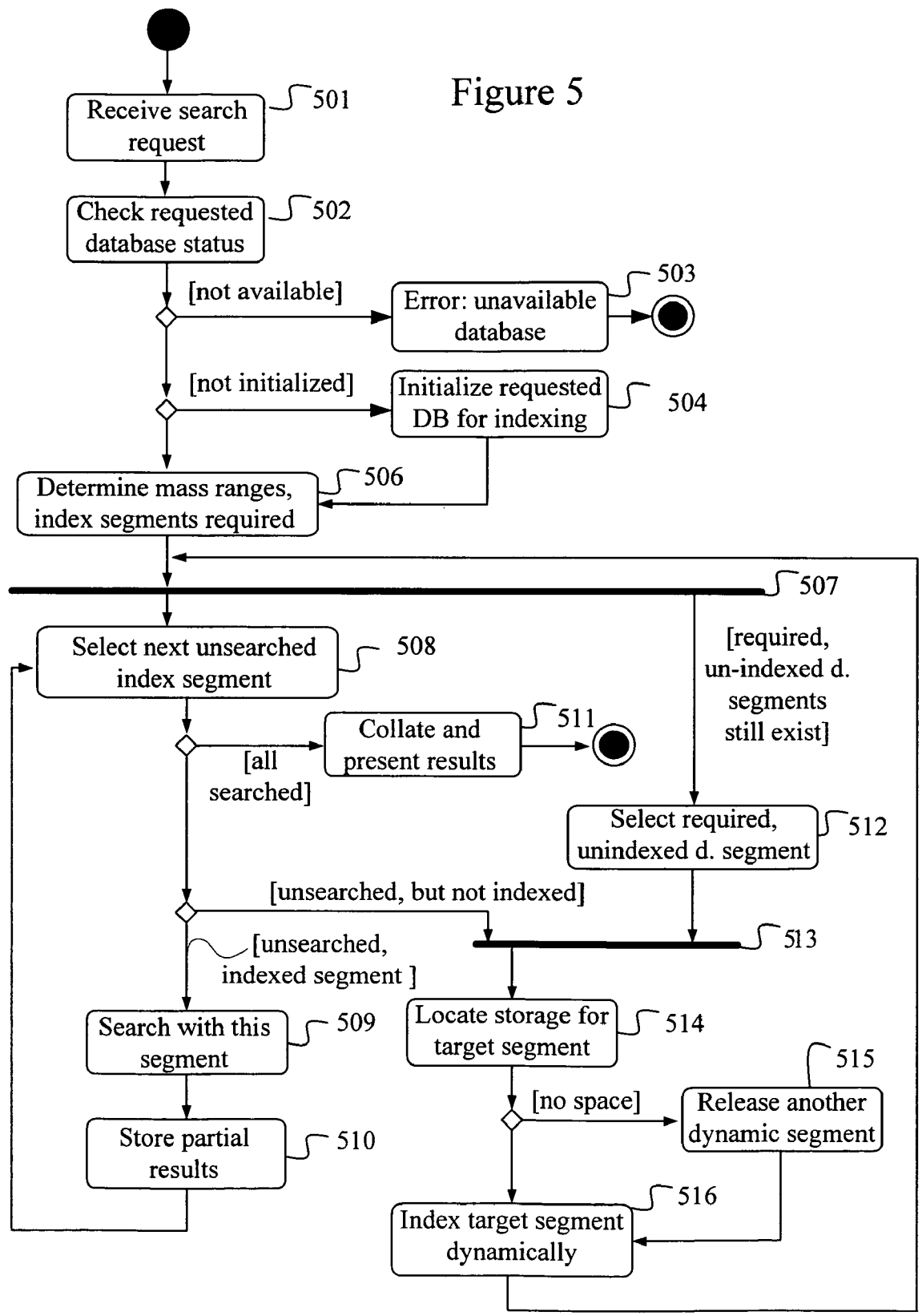

|  | Dataset | Pattern | Index |
|---|---|---|---|
| 601 | Collection of text documents | At least one character string | Based on words of text documents |
| 602 | Derived from set of images | At least part of an image | Based on features of the images |
| 603 | Derived from a set of measured signals | At least part of another signal | Based on properties of the measured signals |
| 604 | Represents a set of molecular structures | At least part of a molecular structure | Based on a geometry or a topology of the molecular structures |
| 605 | Set of sequences representing proteins, DNA, RNA, or other biological molecules | All of a sequence, part of a sequence, or an alignment of sequences | Based on substrings of the sequences |
| 606 | Set of sequences representing proteins, DNA, RNA, or other biological molecules | Range of molecular masses corresponding to a molecule of interest | Based on masses of substrings of the sequences in the dataset |

Figure 6

INDEXING USING CONTIGUOUS, NON-OVERLAPPING RANGES

RELATED APPLICATIONS

This application claims priority of U.S. Provisional Patent Application 60/586,544, entitled "Searching Large Data Sets For Matching Patterns Using A Dynamically Constructed Index Organized Into Contiguous, Non-Overlapping Ranges" filed Jul. 8, 2004.

BACKGROUND OF THE INVENTION

1. Field of the Invention

The present invention relates generally to computer-based matching of patterns in quantitative and symbolic data, and in particular to searching large data sets for matching patterns using a dynamically constructed index organized into contiguous, non-overlapping ranges.

2. Description of the Related Art

A common problem in information retrieval is to find all documents in a large collection or entries in a large database that match a given pattern. Many of the specific pattern-matching problems and solutions thereto that are discussed in the computer science literature arise in text processing, because text data is voluminous, important in commerce and science, and straightforward to represent, if not to analyze. However, pattern matching in large data sets is also an important need in applications of biometric analysis, image analysis, data mining, Internet searching and bioinformatics.

For example, one large-scale analysis is to find all documents with certain keywords in a large corpus, say a database of all U.S. patent descriptions. One method of performing this analysis could include string searching, which is a well-characterized paradigm with several well-known algorithms addressing it. In a string-search, all documents are scanned to look for the matching terms. In some cases, the processing time for the scanning is directly correlated to the length of the database. However, with large datasets, this processing time is not fast enough to respond interactively for a new query.

Therefore, ways of pre-processing the database to support faster response times have been sought. An exemplary pre-processing tool is an "inverted file" index. This inverted file index, which can be maintained in some quickly accessible, ordered data structure, contains all the potential keywords and their locations in the original database. Using such an index, search terms can quickly be looked up and relevant documents located, albeit at the expense of a lengthy pre-processing step and of substantial extra storage (often exceeding the length of the original file).

Despite these disadvantages, most mainstream applications in text searching tend to use an inverted file index to deliver practical performance. Exemplary applications include commercial information systems (e.g. Dialog and Lexis-Nexis), Internet search engines, and toolkits for relational database management system platforms.

Unfortunately, because of the overhead associated with full indexing, an inverted file index may not be completely up to date when it is used. Moreover, the space requirements for the inverted file index leads to pressure to limit its contents. Consequently, frequently occurring words, e.g. articles and prepositions, are often left out. This exclusion may not significantly impact the specificity of a search term in itself, but can reduce the informativeness of a context containing those words.

The field of biomolecular sequence analysis adds new challenges to database pre-processing. Specifically, the growth of DNA and protein sequence databases has fuelled algorithmic developments for mining this data. For example, GenBank is a DNA database containing approximately 36 terabytes of sequence information, 90% of which has been listed in the last 5 years.

The superficial appearance of these sequence databases is as a collection of structured text documents. Although some early methods for sequence analysis were essentially recast string matching algorithms, a class of powerful new methods emerged that met the particular needs of sequence analysis. Particularly important among these were methods for similarity searching, i.e. finding sequences that had patterns in common with a test sequence, wherein the test sequence can be used for inferring homology. However, to model homology well and find evolutionarily divergent related sequences in the database, an algorithm must tolerate a degree of divergence significantly greater than any need that arises in text searching.

A good example of such an algorithm is the Smith-Waterman dynamic programming algorithm. Unfortunately, even with optimization, the speed of the Smith-Waterman dynamic programming algorithm is quadratic in the size of the database (as opposed to the near-linear performance of the string-matching algorithms discussed above). Therefore, the use of the Smith-Waterman dynamic programming algorithm for comprehensive sequence databases remains commercially impractical.

Consequently, there has been an increased interest in the inverted file index approach, even if it lacks the full sensitivity of, for example, the Smith-Waterman dynamic programming algorithm. For example, BLAST (Basic Local Alignment Search Tool), which is a common indexing tool, is based on using an index of all n-mer (wherein n-mer is any string of n characters) subsequences of the source database. The choice of n (for example, n is typically 3 for protein and 11 to 13 for DNA) is a balance between search speed and sensitivity. By reducing n, the algorithm approaches the sensitivity of Smith-Waterman dynamic programming algorithm, but its speed advantage is seriously eroded and there will be a lot more references to follow for each n-mer index entry. Another disadvantage of the BLAST indexed approach compared to Smith-Waterman is the time-consuming process involved in building the index in the first place. Specifically, because BLAST is in essentially a sequential scan, it could significantly accelerate performing the second and subsequent searches, but could take an unacceptable period of time to perform the first search.

In another type of search performed in biomolecular analysis, similar protein sequences are compared on the basis of observed and predicted mass spectra derived from those sequences. Mass spectrometry (MS) has recently become a common and powerful tool for protein analysis, particularly for characterizing novel proteins. In MS, the amino acid sequence of such proteins is obtained.

However, rather than analyzing proteins directly, MS is often applied to peptides derived from the protein(s) of interest. Peptides are generally easier to handle and more suited to the resolving power of mass spectrometers. Cleavage enzymes can cut the protein at specific amino acids and thereby can yield some information relating to the protein. Further, with shorter sequences, the more limited the number of amino acid combinations that can yield the observed mass/charge values, thereby facilitating sequence interpretation.

However, the MS of peptides obtained from proteins (e.g. using tryptic digestion), is not enough by itself to unambiguously determine the sequence of those peptides. Therefore, further information is required. In one approach, called Peptide Mass Fingerprinting (PMF), no further experimental analysis is required. Instead, PMF depends on combining data for all the peptides derived from a protein, and comparing that data to known proteins. Another approach, based on tandem MS, seeks to elicit more information about each individual peptide so that its sequence can be estimated. These approaches will now be further described.

In PMF, masses for the entire set of peptides derived from a protein are compared to a set of masses predicted from peptide sequences. These predicted peptide masses (called a spectrum) are generated computationally from known protein sequences. If most predicted peptide masses match the observed masses (within some tolerance for experimental error), then the parent proteins are putatively considered to match. Typically, in the absence of any further contextual knowledge, the new protein is compared in turn to each of a comprehensive collection of known (or predicted from DNA coding sequences) protein sequences such as SWISS-PROT, TREMBL or NR (NCBI's non-redundant database for protein sequence searching).

The main steps for PMF are as follows. Preprocess peak list (threshold, filter, normalize, etc.) and determine potential peptide ion mass/charge values. For every database protein sequence, (1) perform in-silico analysis of database sequence and calculate mass of peptide fragments, (2) compare observed masses of all peptides to all of the peptide masses calculated from database (within a certain tolerance), (3) score matches by certain algorithm-dependent criteria, and (4) retain candidate matches. Finally, a list of candidate matches can be sorted, ranked, and presented according to score.

In tandem MS, more sequence information is derived for each individual peptide, thereby allowing reconstruction of the protein sequence. Specifically, peptide ions separated by first-stage MS are individually further fragmented. The second-stage MS of those fragments is a convenient, automated method of analyzing each of those peptides.

The steps for tandem MS analysis of peptide fragment ions are as follows. Determine mass and charge of precursor ion from $1^{st}$ stage MS. Preprocess tandem MS peak list (threshold, filter, normalize, etc.) and determine potential fragment ion mass/charge values. For every database protein sequence, (1) perform in-silico digestion of database sequence and calculate mass of peptide fragments, (2) compare observed mass of precursor peptide to each of the peptide masses calculated from database sequence for a match (within a certain tolerance), and (3) for every peptide in the database sequence that matches, (a) predict the fragmentation pattern and thereby the expected tandem mass spectrum for that peptide, (b) compare preprocessed experimental spectrum to computationally predicted spectrum for database peptide sequence, (c) score peptide matches by certain algorithm-dependent criteria, and (d) retain candidate peptide matches. Finally, a list of candidate matches can be sorted, ranked, and presented according to score.

Because fragmentation tends to occur in predictable sites between residues along the peptide backbone, and assuming there is good representation of pairwise fragmentation of the peptide between all adjacent pairs of amino acids, a "ladder" can theoretically be obtained from the mass spectrum. In this mass spectrum, each ion peak is separated from an adjacent peak by the mass corresponding to a single amino acid. Knowing the expected mass associated with each type of amino acid means that the sequence can be inferred.

However, due to noise, contaminants, imperfect representation, unpredictable cleavages, protein modifications, experimental error, multiple charges, and other variables, there are potential problems with reliably ascertaining the sequence of the peptides. Consequently, even with the extra information provided by tandem MS, researchers may still choose to compare the peptide spectra to protein sequence databases. In this case, each spectrum is derived from a single peptide sequence and its likely fragmentation patterns.

Note that in both PMF and tandem MS analysis, at least a comparison by mass of every measured peptide ion to every peptide predicted from every database sequence must be performed. This step presents an opportunity for speed-ups through efficient implementation, because it is in this step that the number of candidate peptides is greatly reduced. Moreover, although the subsequent detailed observed-to-predicted spectrum comparisons involve more computations individually than peptide mass comparisons, the peptide mass comparisons only need to be done for a small fraction of the database.

However, the comparisons of observed spectra to predicted spectra are necessarily approximate, because of biological variation and sample preparation artifacts, experimental error and variability in the MS measurements, database incompleteness and errors, and imperfect models for predicting the spectra from peptide sequences. Therefore, the algorithms that are used for making the comparisons must be sensitive, comprehensive, and error-tolerant-characteristics that, together with the very large number of peptide mass comparisons discussed above, make them computationally intensive and slow on large data sets.

Tandem MS analysis, which can generate thousands of spectra for one original sample, can be especially slow. For example, a typical laboratory-class PC computer available to researchers for MS data analysis may be equipped with a 2.5 GHz Pentium processor and 256 MByte of RAM. Using such a computer, a comparison of a single experimental spectrum may take several seconds against all sequences in SWISS-PROT, which is a highly curated and therefore condensed set of known protein sequences. More comprehensive databases such as the NCBI non-redundant protein sequence database would lengthen the search commensurately. These times compare with modern tandem MS instruments being capable of generating several spectra in every second of operation.

Unfortunately, this slow analysis time is compounded by the exponential growth rate of many sequence databases. Even SWISS-PROT, the rate of growth of which is constrained by its policy of rigorous curation, has nevertheless quadrupled since the first programs for Tandem MS-based protein database searching appeared (i.e. in about 10 years). Indeed, because of recent increases in genome sequencing and analysis projects, some of the more lightly or automatically annotated sequence databases have been growing much faster, and are now orders of magnitude larger than SWISS-PROT.

The combination of more rapid MS data generation and larger databases threatens the practicality of running protein identification programs routinely on laboratory-class PC-type computers. A partial solution has been to recognize that with multiple experiments that need to be analyzed in the same way, comparisons against the same database entries occur repeatedly, and so a speed-up can be obtained by preprocessing the sequence data. In particular, the peptide sequences that are derived from each protein sequence under a given proteolytic digestion scheme can be generated and the associated peptide mass can be pre-computed prior to any comparison with experimental spectra. Furthermore, those masses and references to the associated peptide sequences can be sorted and indexed by mass. In this manner, the comparison to any measured peptide involves comparing those index entries within a narrow mass range, i.e. the index entry centered on the observed peptide mass and extending to those index entries within an expected error. Therefore, the sorting and indexing by mass can significantly reduce the analysis time as now discussed.

In one exemplary operation, a peptide index is generated by modeling a tryptic digest of protein sequences from a database (e.g. SWISS-PROT) in which protein sequences are cleaved in silico (i.e. modeled computationally) after the amino acids lysine (K) and arginine (R). Because missed cleavages are experimentally common, those missed cleavages are modeled up to some limit. For example, peptides containing one or two internal Ks/Rs are also generated.

For a given parent protein sequence database, the size of the peptide index can be measured or estimated. For example, SWISS-PROT Release 43.5 currently has about 56 million amino acids of sequence, of an average length of 370 amino acids each, of which about 11% (every $9^{th}$ amino acid on average) are K or R. In this case, ignoring end-effects due to the sequence actually being divided into 153 thousand discrete protein sequences, and assuming no missed cleavages, the number of generated peptides can be roughly estimated as the total number of amino acids divided by the interval between successive cleavage sites, i.e. 6.2 million in this example. Additionally if one or two missed cleavage cases are considered, then there will be nearly as many entries again for each case. Therefore, the total number of entries with up to 2 missed cleavages is about 18 million. If it is assumed that an index entry must consist minimally of a 4-byte fixed-point mass value together with a 3-byte pointer to parent protein sequence and a 1-byte peptide length field, then such a peptide index will need about 150 Mbytes of system RAM to represent it for rapid access in the database searching programs.

Several programs have used such indexes for MS analysis of peptides. These programs include MOWSE (Molecular Weight Search software developed by Darryl Pappin and Alan Bleasby that can be used for PMF analysis) and Turbo-SEQUEST (protein identification software from Thermo Electron Corp. that can be used for tandem MS analysis).

As described above, a tryptic digest of SWISS-PROT approaches the upper limit of the memory available (allowing for operating system and application software overhead) of a computer with 256 Mbytes of RAM. Doubling or quadrupling this amount of memory will allow for some growth in the databases and/or for more enzymes that cut more frequently.

However, order-of-magnitudes expansion of the storage requirements may still occur. First, storage requirements may significantly increase when source databases are much larger than the 153,000 entries in the SWISS-PROT database. Such source databases include, for example, the NCBI non-redundant database currently including 1.8 million protein entries or the human portion of the dbEST database currently including 5.6 million mRNA-derived entries. Second, storage requirements may also significantly increase based on decreased constraints. Specifically, because proteolytic digestion is in practice imperfect, it is desirable to generate predicted peptides with at least one end unconstrained to specific cleavage sites. This constraint reduction explodes the number of generated peptide sequences retained in an index.

These two cases are beyond the capacity of standard laboratory computers. Additionally, these cases significantly increase the time required to do the in-silico generation of peptides and subsequent indexing. Because of the expense, complexity, and maintenance requirements of supercomputing installations, it is preferable to avoid the route of scaling the hardware to match the larger database sizes.

Therefore, a need arises for a database comparison method suitable even for standard computers. Preferably, this database comparison method can work with smaller portions of the index depending on the experimental data, yet continue to be well matched to the spectrum acquisition rate of the MS instrumentation.

Similar considerations apply to the indexed searches for text-based information retrieval and to BLAST-style indexed sequence similarity searching. In both cases, there are constraints on the index that are due to the size of the source databases. Those constraints may lead to compromises on the contents of the index (e.g. references to frequently occurring words, or the n-mer size for BLAST indexes) and hence to reduced sensitivity or recall in searches using those indexes.

Therefore, a further need arises for a means of searching large datasets efficiently as in an indexed approach, but without the burdensome storage space, index-building run-time, and latency to first search requirements of a full index search.

SUMMARY OF THE INVENTION

A method of efficiently constructing and using an index for searches in large datasets is provided. This method is applicable to a broad variety of search and retrieval problems in datasets arising in text analysis, commercial databases, Internet content, and scientific data collections. Exemplary applications include, but are not limited to, an inverted file text search, a biomolecular sequence similarity search, and MS-based protein/peptide identification.

In this method, "partial" indexing can be used to minimize the initial index time and storage needs. For this partial indexing, a dataset can be divided into a plurality of "buckets", wherein buckets are contiguous, non-overlapping ranges of values of a chosen (e.g. intrinsic or readily computable) attribute of elements of the dataset. These buckets can be used to construct discrete index segments. Specifically, in accordance with one aspect of the invention, "static" index segments associated with "static" buckets are always computed, wherein the static buckets include the more frequently occurring values. In contrast, "dynamic" index segments associated with "dynamic" buckets can be generated on an as-needed basis, wherein the dynamic buckets include the less frequently occurring values.

Designating static and dynamic buckets and selective indexing of the buckets based on this designation can advantageously eliminate unnecessary index time and storage space. Specifically, if some, but not all, index segments are needed in any given search, then the search time can be advantageously reduced because less of the complete index needs to be generated and used. Additionally, the storage size for the index segments can be significantly less than that required for a complete index. Frequency of usage or other conditions/factors can determine which dynamic index segments can be deleted to make storage space available for new dynamic index segments. In one embodiment, the index can be refreshed for an updated dataset by regenerating only the static index segments and deleting all dynamic index segments.

In one embodiment, index segments can be built on demand when a pattern is specified. In another embodiment, a data organization can be chosen based on which index segments are likely to be in demand. For example, in the case of multilingual text data, the index is word-based and the data organization could be the source language of each document. If it is known that one language predominates for queries, or can otherwise from the environment be expected for a new query—say English—then that language can be indexed first. For a monolingual application, index segments could be organized based on different technical vocabularies if the content is technical, or by commonly occurring words if the text is non-technical. In the case of BLAST, the index entries will be based on n-mers in the source database, but some n-mers will be more frequent than others based on known characteristics of amino acid frequency and combinations. Such frequently occurring n-mers can be chosen for static indexing.

Partial indexing can advantageously facilitate searching for matching mass spectra of peptides in a long protein sequence database. In accordance with one embodiment of the invention, a mass-based peptide index can be constructed by dividing what would be the complete index into non-overlapping mass ranges. At this point, certain mass ranges can be completely preprocessed into index segments for searching and a search can be started on one or more mass ranges before all index segments are generated. Specifically, the mass ranges selected for earliest completion of preprocessing and/or for earliest use in searching are those, including error tolerance, of the measured peptide mass or masses of interest. In the case of tandem MS analysis, the mass ranges selected for earliest completion are those of the precursor ions.

Note that peptide sequences can be computationally determined from the protein database sequences, the corresponding molecular masses can be calculated, and index entries can be constructed that include the mass as well as access to the peptide sequence. Further note that the peptide sequence can be stored directly in an index entry or a pointer to the location storing the peptide sequence can be included in the index entry.

Therefore, in accordance with one aspect of the invention, an index segmented by mass range can be constructed, wherein each segment can be constructed and used independently for searching. In one embodiment, those segments required for a particular mass search, i.e. more critical index segments (referenced as the static index segments), can be constructed before other less critical segments (referenced as the dynamic index segments) and even before the generation of the less critical index segments is complete. The generation of the less critical index segments can be advantageously deferred until computational resources are available, i.e. no longer required for the critical index segments.

Certain mass ranges may be more commonly observed in certain experimental conditions and given particular instrumentation. These mass ranges can advantageously form the basis of static index segments, i.e. those segments that should always be available in the index and are not released to make way for dynamic index segments.

Partial indexing increases analysis speed because the latency time to initiate a new search for a peptide of a given mass is reduced to, at most, the time to create the mass ranges of the index that contain that given mass within a certain error tolerance. The capacity of the system for larger databases is also improved because the segmentation of the index means that index creation and mass searching only require system resources (e.g. RAM) that are matched to the size of the largest index segment, instead of to the complete index.

In one embodiment, different index segments can be generated on multiple processing devices, thereby enabling further speed improvements through parallel processing. In yet another speed improvement embodiment, the construction of the index can be executed on a first processing device (i.e. a standard PC system processor or a system including an FPGA performing at least some of the functions of a processor), while a second processing device can perform the search. In the case of a peptide mass search, the second processing device can accept a preprocessed peak list as well as a peptide index segment through DMA, and can return raw results, again through DMA, for post-processing and presentation that can be performed on the first processing device.

BRIEF DESCRIPTION OF THE DRAWINGS

FIG. 3A illustrates a schema for an index entry for a dynamically indexed database of peptide sequences according to one embodiment.

FIG. 3B illustrates the application of the schema of FIG. 3A on sample data.

FIG. 5 illustrates an activity diagram representing the flow of control for searching an indexed database of peptide sequences in a method for mass-searching of peptides measured by mass-spectrometry.

FIG. 6 indicates the applicability of the partial indexing technique to various datasets.

DETAILED DESCRIPTION OF THE DRAWINGS

Figure 1:
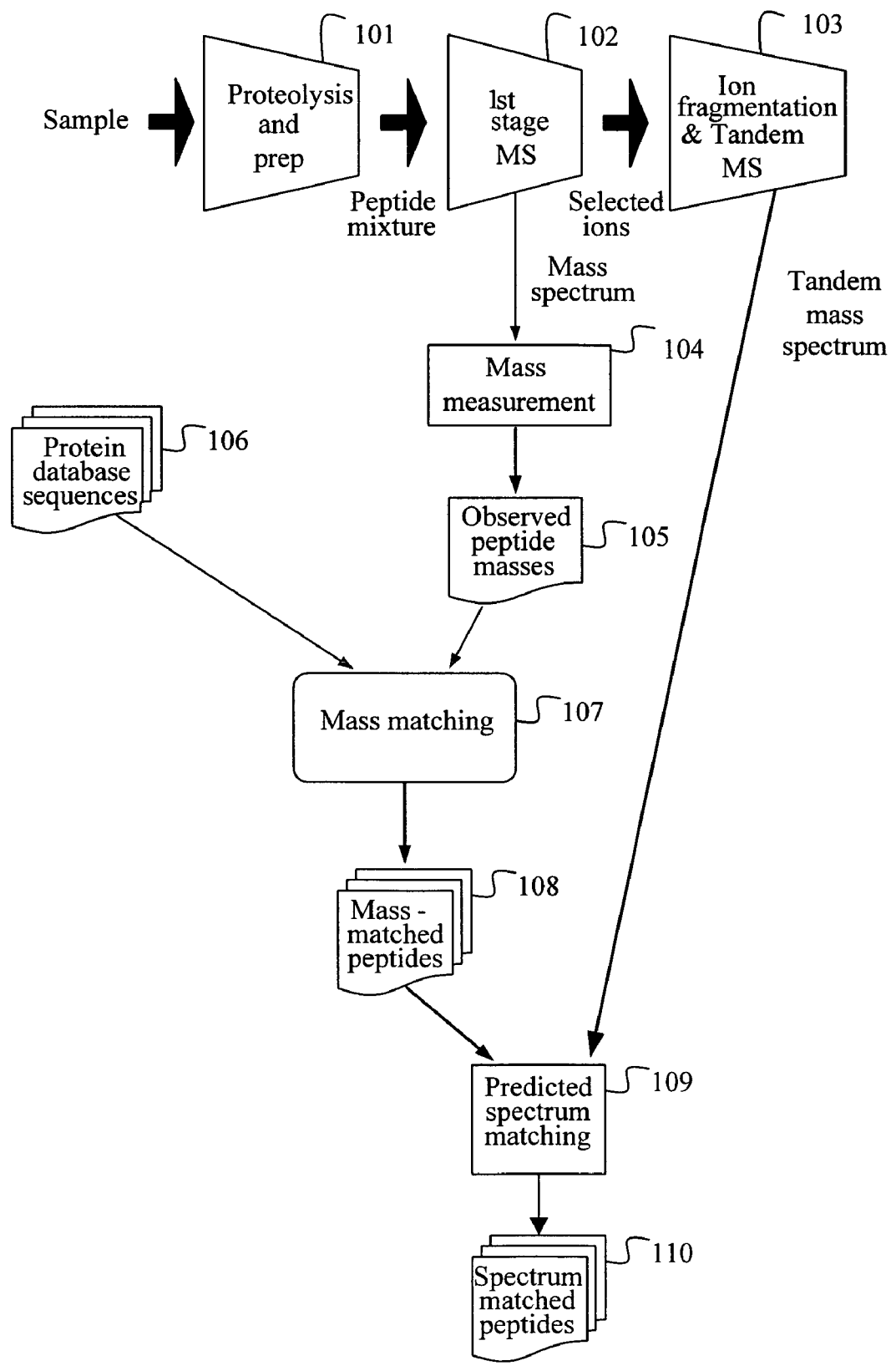
FIG. 1 illustrates a flow chart for protein identification using tandem mass spectrometry.

A method of constructing and using an index for searches in large datasets is provided. This method is applicable to a broad variety of search and retrieval problems in datasets arising in text analysis, commercial databases, Internet content, and scientific data collections. To clarify aspects of this indexing, an exemplary application is now described in reference to FIG. 1, which illustrates a flowchart for identifying proteins through tandem mass spectrometry (MS).

In a sample preparation step 101, a protein sample is broken up into peptides, perhaps by proteolytic digestion with an enzyme such as trypsin, and is made available for analysis in a tandem MS instrument. In first stage MS 102, a mass spectrum is obtained with mass/charge and intensity for ionized peptides. In step 103, ions are fragmented and one or more such ions are selected for tandem MS. Step 103 results in a mass spectrum of the fragment ions derived from each peptide.

Using the mass spectrum obtained in first stage MS 102 and knowledge/estimates of the amount of charge (e.g. using isotopic de-convolution), mass measurement step 104 can derive the observed peptide masses 105 from the measured mass/charge value of an ion's peak. In mass matching step 107, observed peptide masses 105 can be compared to the masses of peptides predicted computationally from protein database sequences 106. These protein database sequences 106 can be provided as a published collection (e.g. SWISS-PROT or NR). Mass matching step 107 can either scan the protein database sequences 106 or use them to build a mass-based index of peptide sequences.

The output of mass matching step 107 is a list of mass-matched peptides 108 (with some allowance for measurement error). Because this list is potentially large and is not generally specific enough to uniquely identify a peptide, a more rigorous comparison can be performed in a predicted spectrum matching step 109. In predicted spectrum matching step 109, each of the mass-matched peptides 108 is used to computationally predict the fragmentation pattern of the peptide and hence the mass spectrum that would be expected in tandem mass spectrometry. That predicted spectrum can be compared to the tandem mass spectrum (output from tandem MS step 103) for a matching pattern. Predicted spectrum matching step 109 outputs a list of spectrum-matched peptides 110, which typically provides a usable short list of candidate matches to the original unknown sample.

Figure 2:
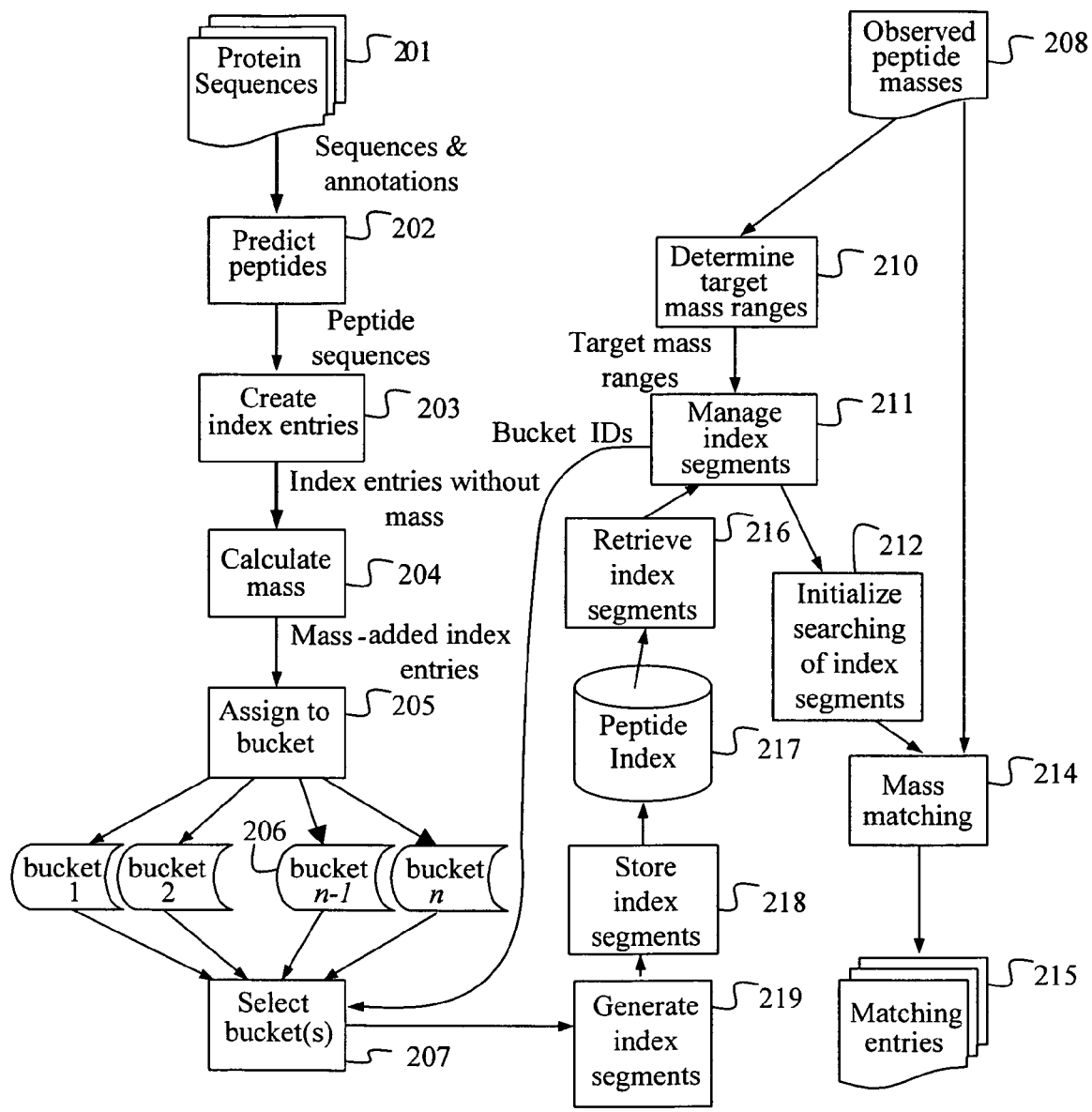
FIG. 2 illustrates a data flow diagram of a method for searching for masses of peptides measured by mass-spectrometry in a dynamically indexed database of peptide sequences according to one embodiment.

FIG. 2 illustrates a flow chart of a method for searching for masses of peptides measured by mass-spectrometry in a dynamically indexed database of peptide sequences. In this method, a set of protein sequences 201 (substantially identical to protein database sequences 106 in FIG. 1) is used, wherein each protein sequence typically includes an associated biological annotation that can be used to describe the matches (i.e. matching entries 215).

Using protein sequences 201, step 202 can predict potential peptide sequences by forming a set of all possible substrings of those protein sequences. In some embodiments, the set can be constrained to reduce its size, e.g. by modeling the effect of a sequence-specific proteolytic enzyme such as trypsin (which cleaves at K and R residues only). These peptide sequences can be associated with index entries in step 203. For each index entry, step 204 can calculate its expected mass based on the molecular weight of the amino acids the peptide sequence comprises. This mass can be associated with its corresponding index entry.

Thus, an index entry can minimally include program access to a peptide sequence and its mass. In one embodiment, this information can be embedded directly in the index entry. In another embodiment, the index entry can reference a separate data structure including the peptide sequence and/or its mass. An efficient data structure, which avoids duplicating sequence data when some of the computed peptides are overlapping, is to use pointer fields in the index entries, wherein each pointer field points to an offset within a representation of the original protein sequences.

FIG. 3A illustrates a simplified index entry 301 that includes a pointer 303 to the start of the sequence of the peptide in a list of protein sequences, a length 302 of that peptide sequence in number of amino acids (an offset to be added to the sequence pointer 303 to fix the end point of the peptide sequence), and a mass 304 that indicates a mass calculated from the peptide sequence. In one embodiment of index entry 301, length 302 is 1 byte, pointer 303 is 3 bytes, and mass 304 is 4 bytes (fixed point number). In other embodiments, index entry 301 can include fewer or more than 8 bytes.

FIG. 3B illustrates the application of the schema of FIG. 3A on sample data. In this application, a protein sequence list 305 contains a list of protein sequences supplied to the method (step 201 in FIG. 2), wherein each line of protein sequence list 305 represents a protein. Peptide index entries refer to substrings (i.e. peptides) of the contents of the protein sequence list 305. Three sample index entries 306, 307, and 308 refer to three peptides in protein sequence list 305.

For example, index entry 306 contains an entry for the first tryptic peptide (i.e. a peptide resulting from a protein being exposed to trypsin, which is a proteolytic enzyme) of the third protein sequence record, i.e. the peptide sequence MDFK. In index entry 306, the sequence pointer contains the file offset in protein sequence list 305 where that subsequence begins; the length is 4 amino acids (i.e. the length of the substring MDFK); and the mass is 539.6532 Da. Similarly, index entry 307 contains an entry for the second tryptic peptide of the third protein sequence record, i.e. the peptide sequence YSDTVIHNGVVFYITDCGHR. In index entry 307, the sequence pointer contains the file offset in protein sequence list 305 where that subsequence begins; the length is 20 amino acids (i.e. the length of the substring YSDTVIHNGVVFYIT-DCGHR); and the mass is 2296.5489 Da. Index entry 308 contains an entry for the third tryptic peptide of the third protein sequence record, i.e. the peptide sequence AYFIYG-GCLLSVPR. In index entry 308, the sequence pointer contains the file offset in protein sequence list 305 where that subsequence begins; the length is 14 amino acids (i.e. the length of the substring); and the mass is 1558.8649 Da.

Note that the protein sequences of protein sequence list 305 typically form a continuous byte stream with terminator characters separating the protein sequences (e.g. in a text file, the terminator character could be a carriage return) and therefore each pointer can identify a unique location (e.g. an offset in the byte stream) for that peptide. In other embodiments, the sequence pointer could include both line (i.e. protein sequence) and offset information. In yet other embodiments, each protein sequence could have its own record, thereby creating a relational database of the index entries.

Similar entries can be computed for all peptides predicted from protein sequence list 305. These entries can be computed using a tryptic digestion model, as described in reference to FIG. 3B, or modeled using a different enzyme or "no-enzyme", wherein the peptides generated are all possible overlapping substrings of the original protein sequences.

Figure 3C:
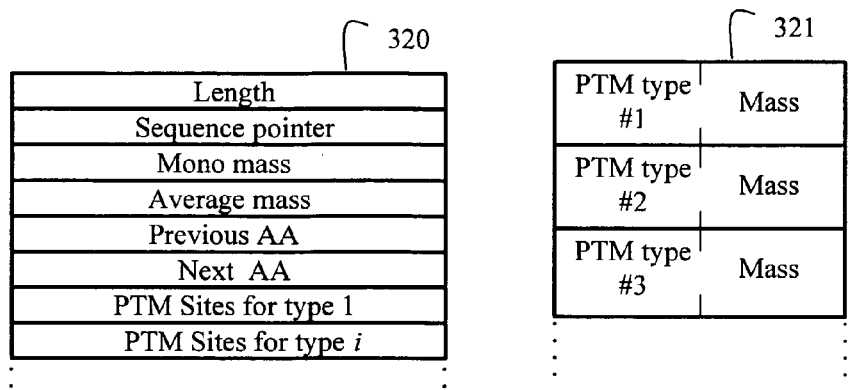
FIG. 3C illustrates a schema for augmenting index entries with further information that enhances post-processing of results.

In one embodiment, the index entries may be augmented with further information that enhances post-processing of the results. This information could include, for example, references to the annotation, the sequence context in which the peptide appears, alternative mass calculations (e.g. mono-isotopic and poly-isotopic average), and potential post-translational modification sites. A schema incorporating such information is illustrated in FIG. 3C. An index entry 320 augments the basic index entry (as illustrated in FIG. 3A) with a further mass field, fields to record the amino acids immediately preceding and following the peptide of interest (to assist with determining enzymatic cleavage conditions), and fields to indicate which sequence characters are susceptible to PTMs of designated types, which are kept in a PTM table 321, with one entry per type of PTM.

Figure 3D:
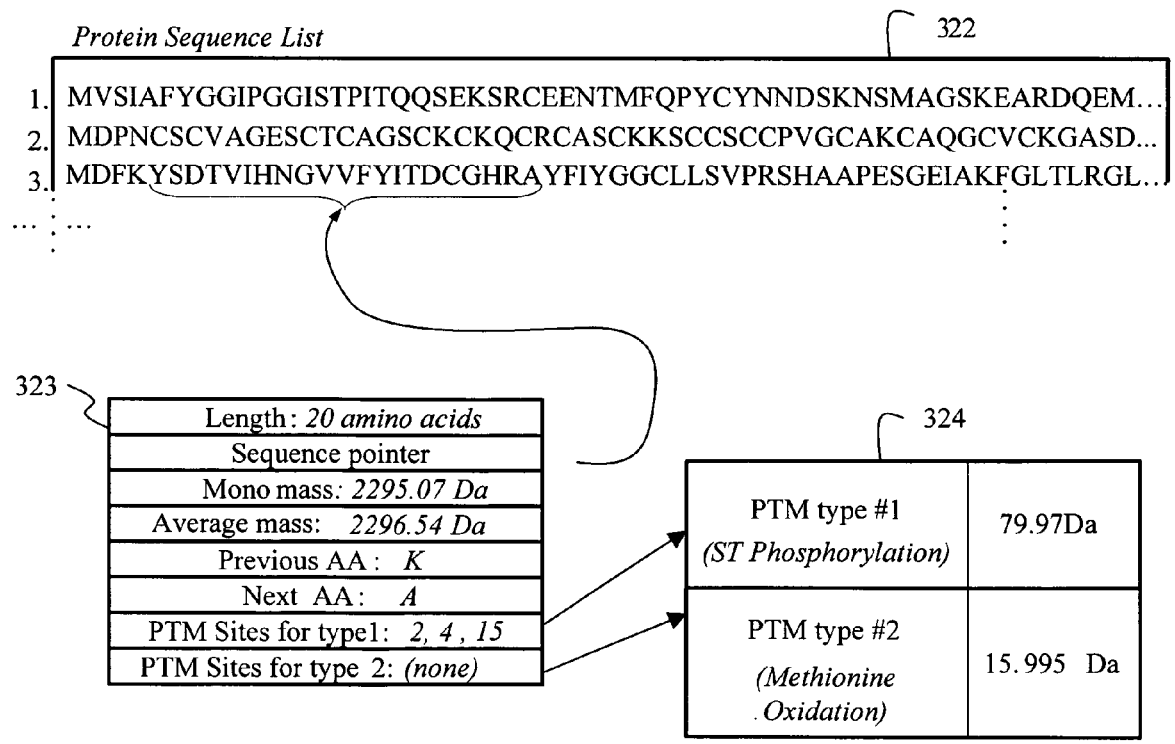
FIG. 3D illustrates the application of the schema of FIG. 3C on sample data.

FIG. 3D illustrates the application of the schema of FIG. 3C with the values determined for the second tryptic peptide of the third protein sequence in a typical Protein Sequence List 322. The entry 323 for this peptide points to its occurrence in the Protein Sequence List, records its length (20 amino acids) and masses calculated using monoisotopic and average element masses, shows that the peptide is preceded by K and followed by A, and notes potential occurrences of PTMs of interest. The PTM list 324 is populated in this example with two PTM types—Phosphorylation at S or T residues (such as residues 2,4, and 15 of this peptide), and Methionine oxidation (no such sites in this peptide) —and the associated mass changes. The index entry records in a separate field for each PTM type the potential occurrences of that PTM type, i.e. in this example, ST Phosphorylation at residues 2, 4, and 15, and no potential M oxidation.

Referring back to FIG. 2, step 205 can advantageously assign each index entry to one of buckets 206 based on its calculated mass. In accordance with one aspect of the invention, buckets 206 can be partitioned using predetermined, contiguous, and non-overlapping mass ranges. These buckets are held ready until they are subsequently selected in step 207 for index segment generation in step 219. Note that an index segment corresponds to one of the predetermined, contiguous, and non-overlapping mass ranges used to construct the buckets 206, and contains a set of index entries within that mass range.

Step 218 can store the generated index segments in a peptide index 217. In one embodiment, peptide index 217 can be organized using a relational database system containing records both corresponding to the individual index entries, as well as an entire index segment containing a list of all the entries in the mass range sorted by mass. Step 216 can retrieve the stored index segments for subsequent searching (described below in reference to step 212).

Step 211 manages any retrieved index segments. In accordance with one aspect of the invention, the index segments are designated either static (i.e. always present in peptide index 217) or dynamic (i.e. loaded into peptide index 217 on demand). Note that certain dynamic index segments may already be present from a previous storing step 218 or they may need to be recreated. In either case, step 211 can advantageously determine which bucket(s) 206 are required. In other words, step 211 of managing the index segments actually controls step 207 of selecting the bucket(s). In one embodiment, step 211 sends the appropriate bucket identifiers to step 207, which in turn retrieves each desired bucket and provides it to step 219 for index segment generation. In one embodiment, each index segment is generated from an unsorted bucket by sorting the entries according to sequence and collapsing entries with duplicated sequence into a single entry (so every peptide sequence in the database is unique).

Therefore, step 211 can either retrieve existing index segments in peptide index 217 or cause desired index segments not in peptide index 217 to be generated. Additionally, step 211 allows/triggers the index segments to be searched in step 212. In one embodiment, step 211 can control the order of this search, e.g. a search on existing index segments can start before all index segments are available in peptide index 217. This control can advantageously speed the entire method up if step 214 of mass matching is performed in parallel to the indexing (step 219) on a separate processing device (e.g. a microprocessor, another type of processor, or a system including an FPGA performing at least some functions of a processor).

Step 211 of managing the index segments can also control which index segments are designated static/dynamic segments as well as determine which dynamic segments should be removed if the space is required for newly created index segments. This removal can be done by automatically using a least-recently-used algorithm or explicitly making the most commonly encountered mass ranges static.

From observed peptide masses 208 (that can be derived from mass spectrometry data), a step 210 can determine the target mass ranges that include a measured mass and nearby masses within an error tolerance. Step 211 determines the index mass ranges that overlap (i.e. straddle) or fall within the target mass ranges. Thus, step 211 identifies the index segments (retrieved in step 216) that contain the peptide entries (together with their computed masses) that are required for mass matching.

Step 212 can initialize the searching of each of the identified index segments, i.e. performs a predetermined peptide selection for the identified index segment. In one embodiment, step 212 can designate a search to begin with the peptide having the lowest peptide mass and can then successively use the peptide having the next highest mass in the index segment. Step 214, which can perform mass matching, uses the results of step 212 as well as observed peptide masses 208 to generate a list of matching entries 215. Matching entries 215 match observed peptide masses 208 within the given error tolerance. Notably, matching entries 215 can be used in the application of FIG. 1. For example, matching entries 215 could replace mass-matched peptides 108 for predicting spectra in step 109. Note that steps 212 and 214 can collectively be called "searching" herein (see FIG. 5, for example).

Figure 4:
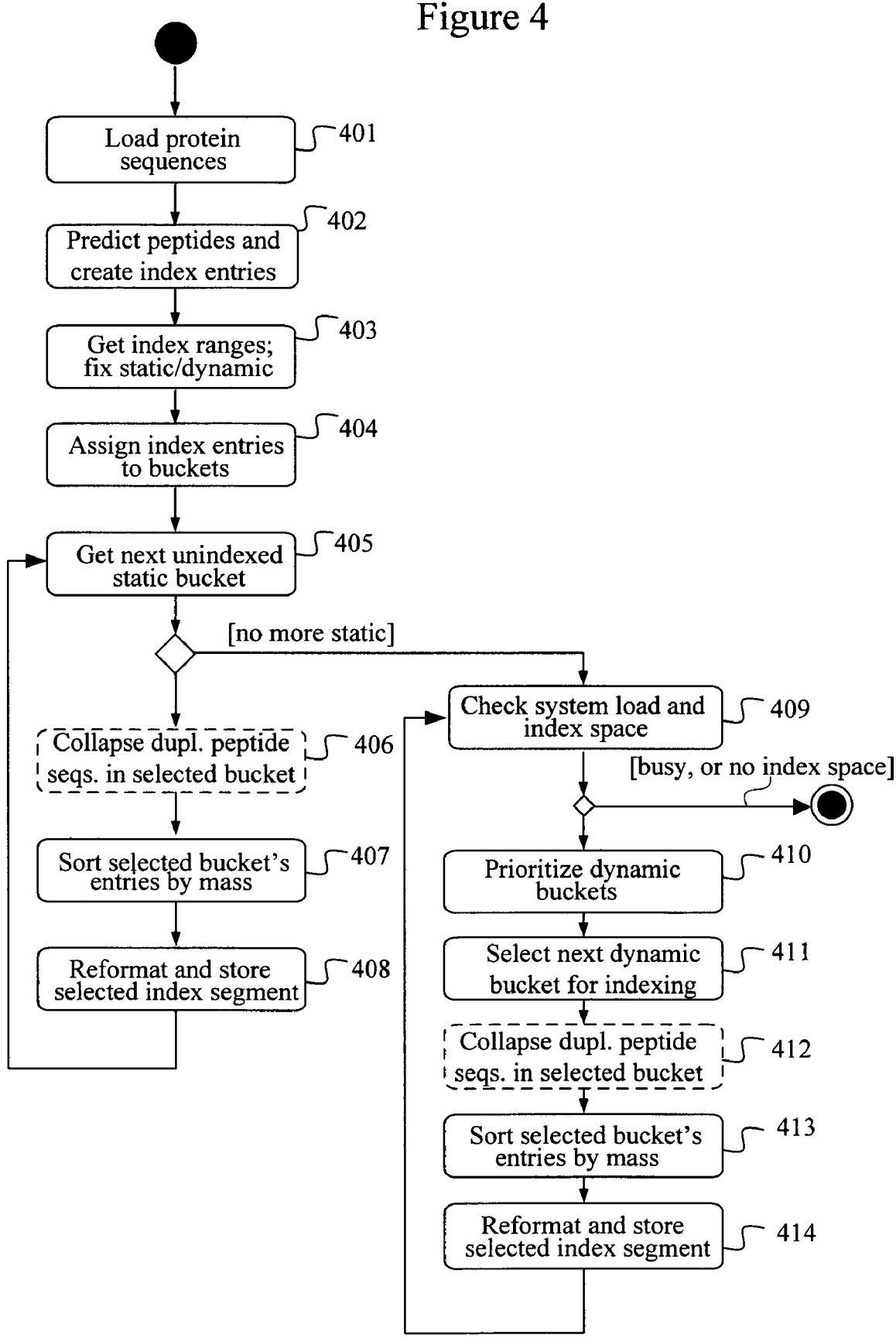
FIG. 4 illustrates an activity diagram representing the flow of control for initializing an index of peptide sequences and masses in a method for mass-searching of peptides measured by mass-spectrometry.

FIGS. 4 and 5 illustrate certain aspects of the control flow used in the partially configured index method. Specifically, FIG. 4 illustrates an activity diagram representing the flow of control for initializing the index of peptide sequences and masses, whereas FIG. 5 illustrates an activity diagram representing the flow of control for searching with that index.

For index initialization, step 401 can first load the protein sequences that form the search database (referenced as protein sequences 201 in FIG. 2 and protein sequence list 305 in FIG. 3). Step 402 can predict peptide sequences computationally and create the mass-added index entries (referenced as steps 202-204 in FIG. 2). In step 403, a scheme is provided for establishing the index ranges as well as for designating which ranges are to be indexed dynamically and which statically.

In one embodiment, designating static/dynamic indexes includes determining more frequently occurring values (e.g. using empirically-derived information) and designating such values for static indexing. Less frequently occurring values can be designated for dynamic indexing. Based on this static/dynamic designation, each bucket can be characterized as either a static bucket or a dynamic bucket. Step 404 can assign index entries to buckets (referenced as step 205 in FIG. 2). In another embodiment, designating dynamic/static indexes can further include comparing the observed mass ranges to the buckets, thereby facilitating a "learning" process that responds to actual masses.

Prior to searching with this database, the static index segments must be generated. Therefore, in step 405, each bucket to be indexed as a static index segment (i.e. each static bucket) is selected until there are no more static buckets remaining. For each static bucket selected to be indexed, step 406 first sorts the entries by sequence to find duplicate sequences and collapse those duplicate peptide sequences. Step 407 can then sort the remaining entries by mass for subsequent rapid lookup/searching. These results can be reformatted and stored in step 408 for subsequent retrieval and searching.

Note that step 406, while optional, can be a valuable technique for reducing the size of the index and the amount of searching required (i.e. because multiple entries corresponding to duplicate sequences can be collapsed into a single representative entry). In one embodiment, by retaining multiple references to the parent protein sequences from which each of the duplicate peptide sequences was derived, that information can be retained. An exemplary and convenient mechanism for this bookkeeping is to use a relational database system in which a first table contains records corresponding to the index entries as stored in an index segment and a second table contains records describing all the protein sequence contexts in which those peptides arise.

If, at the decision point following step 405, there are no more un-indexed static buckets of index entries, then the system can be configured to start indexing dynamic buckets in anticipation of their being needed for a later search. In one embodiment, this indexing of dynamic buckets will occur only if system resources are available. Therefore, in step 409 a system check can be performed.

If the system is busy because a search request has been received or if there is no further index space available in any case, the index initialization process is considered complete, as indicated by the exit from the activity diagram. Alternatively, as long as the system is otherwise idle and space remains to build dynamic index segments, then the method proceeds to do so. In step 410, the remaining buckets, i.e. the un-indexed dynamic buckets, are prioritized. For each such dynamic bucket selected by step 411, the bucket can be indexed similarly to the static buckets, i.e. the entries can be optionally collapsed to remove duplicates in step 412, sorted by mass in step 413, and reformatted and stored as an available dynamic index segment in step 414. These steps can be repeated for further un-indexed dynamic buckets assuming that resources remain available.

FIG. 5 illustrates an activity diagram showing the sequence of events when a new search request is received in step 501. Such a request includes the mass data to be searched, the database and peptide index to which it is to be compared, and other parameters that control details of the algorithm. These parameters could include, for example, amino acid mass values to be used for computing peptide masses, how to look for post-translational modifications, the error tolerance to be used in mass-matching, and score thresholds and cut-offs for reporting results. Step 502 can perform a check on the status of the database and the peptide index that has been requested.

If the requested database of protein sequences (referenced as protein sequences 201 in FIG. 2) has not been loaded onto the system, then the search cannot be executed. In this case, an error can be generated 503, thereby terminating the search request. If the database has been loaded, but the index of derived peptides has not been generated, then the index initialization process shown in FIG. 4 can be invoked. After the index segments of derived peptides is available/generated, step 506 can determine the target mass ranges and thereby the index segments that will be required to carry out the search.

In one embodiment, shown in FIG. 5, there can be a parallel flow of control indicated by a fork of control 507. Specifically, searching can proceed in steps 508-510, while the indexing of dynamic buckets can proceed in steps 512-516 (e.g. if there are index segments that are desired for searches but not immediately available because they have not yet been built). In one embodiment providing maximum parallelism, independent processing resources may be made available for searching and dynamic indexing. In other embodiments, searching and dynamic indexing can share processing resources.

The searching process can start by selecting an unsearched index segment in step 508. If all index segments are searched, then step 511 can collate and present the search results. At this point, the search request terminates.

If there is an unsearched index segment, then step 509 can search with that index segment. Step 510 can store the results of this search (called a partial search in relation to the full index search). At this point, steps 508-510 can be repeated until an unsearched index segment is found that is not indexed. If a segment to be searched is not yet indexed, then the search thread of control joins the indexing thread of control as denoted by a join 513.

The first step in the indexing of dynamic buckets is to select an index segment that is required for the search that has not been indexed yet, either from a selection step 512 or because it has been just selected for search 508. After identifying a segment to be dynamically indexed, step 514 can locate the space for it. Note that no space may be available because a goal of the indexing technique is to create a searchable index in limited space. In this case, step 515 can "release" another dynamic index segment (e.g. deleting that dynamic index segment from peptide index 217) to create the necessary space. Although this release can be done arbitrarily, heuristics such as a least-recently-used algorithm may be used to improve efficiency and to ameliorate the chances for re-using an already indexed segment. Space having made for it, step 516 can create the required dynamic index segment (e.g. using steps 412-414 of FIG. 4). At this point, the process can return to fork of control 507 for further index segment creation or index segment searching.

Although illustrative embodiments have been described in detail herein with reference to the accompanying figures, it is to be understood that the invention is not limited to those precise embodiments. They are not intended to be exhaustive or to limit the invention to the precise forms disclosed. As such, many modifications and variations will be apparent to practitioners skilled in this art.

For example, the above-described indexing technique can be equally applied to various datasets as shown in FIG. 6. If the dataset is a collection of text documents, then the pattern could include at least one character string and the index could be based on words of the text documents (601). If the dataset is derived from a set of images, then the pattern could be at least part of an image and the index could be based on features of the images (602). If the dataset is derived from a set of measured signals, then the pattern could be at least part of another signal, which is either measured or predicted, and the index could be based on properties of those measured signals (603). If the dataset represents a set of molecular structures, then the pattern could represent at least part of a molecular structure and the index could be based on a geometry or a topology of the molecular structures (604). If the dataset is a set of sequences representing proteins, DNA, RNA, or other biological molecules, then the pattern could represent all of a sequence, part of a sequence, or an alignment of sequences and the index could be based on substrings of the sequences (605). If the dataset is a set of sequences representing proteins, DNA, RNA, or other biological molecules, then the pattern could represent a range of molecular masses corresponding to a molecule of interest and the index could be based on masses of substrings of the sequences in the dataset.

Accordingly, it is intended that the scope of the invention be defined by the following Claims and their equivalents.

The invention claimed is:

1. A method for constructing and using an index in searches for matches in a dataset to a pattern, the method comprising:
   dividing the dataset into buckets, wherein buckets are contiguous, non-overlapping ranges of values of a chosen attribute of elements of the dataset;
   specifying a pattern for which a match range of values of the chosen attribute can be determined and against which entries in the dataset are to be compared;
   determining a range of values based on a frequency of anticipated occurrence;
   generating a first set of values based on being within the range, the first set being a static set;
   generating a second set of values based on being outside the range, the second set being a dynamic set;
   identifying a set of static buckets corresponding to the static set;
   identifying a set of dynamic buckets corresponding to the dynamic set;
   generating a first set of index segments corresponding to the set of static buckets;
   generating a second set of index segments corresponding to the set of dynamic buckets;

performing a first search by using the first set of index segments;

performing a second search by using the second set of index segments only when index space is available; and recording which of the second set of index segments is less frequently used, thereby allowing such index segments to be released to make way for dynamic index segments if a needed index segment of the second set of index segments is not currently available.

2. The method of claim 1, wherein generating the second set of index segments and performing the second search are performed on separate processing devices.

3. The method of claim 1, wherein generating the first set of index segments is performed using more than one processing device.

4. The method of claim 1, wherein more than one processing device is used for generating the first and second sets of index segments.

5. The method of claim 1, wherein generating the first and second sets of index segments includes sorting entries of the index segments based on values of the chosen attribute.

6. The method of claim 1, further comprising refreshing the index for an updated database by deleting all of the second set of index segments and only regenerating the first set of index segments.

7. The method of claim 1, wherein
the dataset is a set of sequences representing proteins, DNA, RNA, or other biological molecules,
the pattern represents all of a sequence, part of a sequence, or an alignment of sequences, and
the index is based on substrings of the sequences.

8. The method of claim 1, wherein
the dataset is a set of sequences representing proteins, DNA, RNA, or other biological molecules,
the pattern represents a range of molecular masses corresponding to a molecule of interest, and
the index is based on masses of substrings of the sequences in the dataset.

9. The method of claim 1, wherein the dataset represents peptide sequences derived computationally from protein sequences, where the peptide sequences are modeled as substrings of the protein sequences.

10. The method of claim 9, wherein one or both ends of each peptide sequence model cleavage at certain amino acids by a site-specific agent.

11. The method of claim 10, wherein the site-specific agent includes trypsin.

12. The method of claim 9, wherein the protein sequences are sorted and duplicate sequences are removed or combined.

13. The method of claim 9, wherein the peptide sequences are sorted and duplicates are removed or combined.

* * * * *

UNITED STATES PATENT AND TRADEMARK OFFICE
CERTIFICATE OF CORRECTION

PATENT NO. : 7,962,489 B1  
APPLICATION NO. : 10/982087  
DATED : June 14, 2011  
INVENTOR(S) : David Chiang et al.

Page 1 of 1

It is certified that error appears in the above-identified patent and that said Letters Patent is hereby corrected as shown below:

Title Page
Item (74); change "Bener" to -- Bever --.

Signed and Sealed this
Second Day of August, 2011

David J. Kappos
*Director of the United States Patent and Trademark Office*